United States Patent [19]

Anderson

[11] Patent Number: 4,665,246

[45] Date of Patent: May 12, 1987

[54] METHOD OF PRODUCING ETHYNYL AROMATIC COMPOUNDS

[75] Inventor: Chris Anderson, Salt Lake City, Utah

[73] Assignee: Chem Biochem Research, Inc., Salt Lake City, Utah

[21] Appl. No.: 588,087

[22] Filed: Mar. 9, 1984

[51] Int. Cl.$^4$ ............... C07C 13/00; C07C 15/00; C07C 15/12; C07C 1/30; C07C 1/26; C07C 1/253; C07C 1/26

[52] U.S. Cl. .................. 585/320; 568/319; 568/322; 568/323; 570/182; 570/184; 570/185; 585/24; 585/25; 585/319; 585/321; 585/325; 585/400; 585/469

[58] Field of Search .............. 585/469, 400, 24, 25, 585/319, 320, 325, 321; 570/184, 182, 185; 568/319, 322, 323

[56] References Cited

U.S. PATENT DOCUMENTS

| | | | |
|---|---|---|---|
| 3,923,910 | 12/1975 | Diamond | 570/128 |
| 3,952,067 | 4/1976 | Douglas et al. | 585/320 |
| 3,991,212 | 11/1976 | Marshall et al. | 570/128 |
| 4,016,214 | 4/1977 | Douglas et al. | 585/320 |
| 4,284,834 | 8/1981 | Austin et al. | 585/25 |
| 4,296,264 | 10/1981 | Diamond | 570/128 |
| 4,301,313 | 11/1981 | Marshall et al. | 570/128 |
| 4,374,291 | 2/1983 | Lau | 585/320 |
| 4,528,114 | 7/1985 | Petrzilka | 585/20 |

FOREIGN PATENT DOCUMENTS 1581359 12/1980 United Kingdom ............... 585/20

OTHER PUBLICATIONS

"Friedel–Crafts and Related Reactions," vol. III, Part 1, Olah, G. A., Interscience Pub., N.Y., pp. 20–22, 36–38, 43–44, 62, 108–109, 120, 154–156, 235–239 (1964).

"Organic Chemistry", Morrison, R., et al., 3rd ed., Allyn & Bacon, Inc., Boston, Mass., pp. 458–459, 526–528, 636–637 (1973).

Dabrowski, R., et al., Mol. Cryst. Liq. Cryst., vol. 87, pp. 107–135 (1982).

Sabourin, et al., J. Org. Chem., vol. 48, p. 5135 (1983).

Adomenas, P., et al., Advances in Liquid Crystal Research and Applications, ed., Bata, L., Pergamon Press, Oxford, pp. 1029–1038 (1980).

Primary Examiner—Teddy S. Gron
Attorney, Agent, or Firm—George H. Mortimer

[57] ABSTRACT

The process of producing ethynyl aromatic compounds which are useful as intermediates in the preparation of 3-dimensional carbon-carbon structures for aerospace and military applications and as starting materials in the preparation of organic semi-conductors. The ethynyl aromatic compounds may be any of the classes illustrated in FIGS. 1, 2 and 3 of the drawing. Starting compounds for the process may by any compound from the classes illustrated in FIGS. 4, 5 and 6. The starting compound is reacted in the presence of a Friedel-Crafts catalyst in a suitable solvent with an acyl compound from the class illustrated in FIG. 7 to yield a compound within the classes illustrated in FIGS. 8, 9 and 10. The carbonyl groups in this compound are reduced to yield a corresponding alcohol. Each hydroxy group in the alcohol is converted to an easily eliminatable group, e.g., by reacting it with methane sulfonyl chloride, when subjected to basic conditions. The chlorine and the easily eliminatable groups are then eliminated under basic conditions to yield the desired ethynyl aromatic compound.

Illustrative examples of products produced by the process of the invention include 4-4'-diethynyldiphenyl methane; 1,2-(4,4'-diethynyldiphenyl) ethane; 1,1-(4,4'-diethynyldiphenyl) ethane; tris(4-ethynyl phenyl) methane; 4-ethynyl toluene; 2,2'-(4,4'-diethynyldiphenyl) propane; and 4-ethynyl biphenyl.

10 Claims, 10 Drawing Figures

METHOD OF PRODUCING ETHYNYL AROMATIC COMPOUNDS

INTRODUCTION

The present invention relates to a process of producing ethynyl aromatics which are useful as intermediates in the preparation of 3-dimensional carbon-carbon structures which are used in aerospace and military applications and have been proposed for use as starting materials for organic semi-conductors.

BACKGROUND OF THE INVENTION

The need for light weight ablative materials for aerospace and military applications is well established. An extensive report identified as AFWAL-TR-81-4171, Part II, by D. D. Woolley dated December 1982 entitled DEVELOPMENT OF CARBON-CARBON COMPOSITES WITH IMPROVED CHARRING CHARACTERISTICS describes composite structures and the advantages of these materials. U.S. Pat. No. 4,284,834 gives a good outline of this need and proposes that homopolymerizable diethynyl substituted aromatics be used for this purpose. U.S. Pat. No. 4,374,291 discloses a process of producing a class of such materials defined as bis(ethynylphenyl) compounds which comprises diazotizing particular diphenyl dianalines to form a dihalogenated diphenyl compound, coupling it with ethynyltrimethylsilane in the presence of an organopalladium complex and a ligand to yield an end-protected diphenyl compound having acetylenic moieties thereon, and subsequently removing said end-protecting groups from the diphenyl compound by treating the end-protected compound with a weak base in an inert atmosphere. This process is characterized by low yield and the product, while suitable for the intended purpose, is very expensive.

Processes for preparing certain ethynyl aromatic compounds involving a halogenation operation have been proposed, but such processes are applicable only to starting materials which have no reactive aliphatic hydrogen atoms. Compounds having such reactive hydrocarbons when used in prior art processes give undesirable side products. See, for example, the article by Sabourin et al. entitled A CONVENIENT SYNTHESIS OF 4-ETHYNYLPHTHALIC ANHYDRIDE VIA 2-METHYL-3-BUTYN-2-OL, *J. Org. Chem.* 48, pp 5135 et seq., 1983.

SUMMARY OF THE INVENTION

The process of the invention comprises four steps or operations:

1. Chloroacylation of selected aromatic hydrocarbons in the presence of a Friedel Crafts catalyst to produce materials characterized by the presence of carbonyl groups.
2. Reduction of the chloroacyl derivatives to a chlorohydrin in which the carbonyl groups are converted to hydroxyl groups.
3. Converting the hydroxyl groups in the product of step 2 to easily eliminatable groups.
4. Eliminating the chlorine and eliminatable groups in the product of step 3 under basic conditions to yield the desired ethynyl aromatic compounds.

This process results in high yields of the desired compounds which can be produced for much lower cost than the same compounds can be produced by the prior art process.

A valuable feature of the synthesis of ethynylaromatics by the prosess of the invention is derived from the fact that the process can be applied to the preparation of ethynylaromatics from aromatic hydrocarbons that contain reactive hydrogen atoms which react with many reagents normally used for the preparation of ethynylaromatics to give undesired products.

Another highly desirable feature of the process of the invention is that it is amenable to scale-up.

BRIEF DESCRIPTION OF THE DRAWINGS

The drawings represent chemical compounds in which.

DETAILED DESCRIPTION OF THE INVENTION

Figure 1:
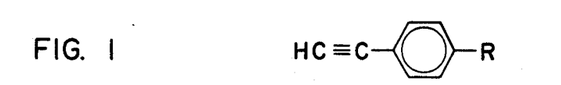
FIGS. 1, 2 and 3 represent classes of compounds produced by the process of the invention.
Figure 2:
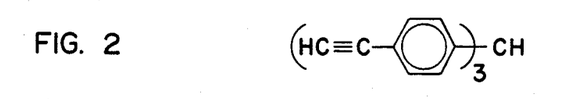
Figure 3:
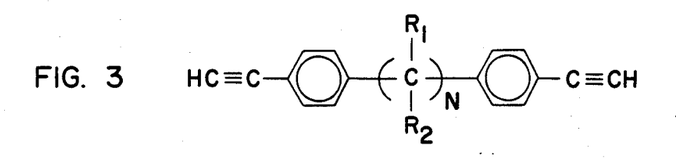

The process of the invention relates to the production of ethynyl aromatic compounds from the classes represented by the structural formulas of FIGS. 1, 2 and 3.

FIG. 1 represents a para-disubstituted phenyl compound, one substituent being the acetylenic group $HC{\equiv}C{-}$ and the other substituent being R which is selected from the group consisting of H, alkyl and phenyl.

FIG. 2 represents triethynylphenyl methane.

FIG. 3 represents a class of diphenyl compounds in which each phenyl ring has two para related substituents, one being the acetylenic group $HC{\equiv}C{-}$ and the other being common to both rings and comprising n methylene groups in which n may be 1 to 4, R1 is selected from the group consisting of H and alkyl and R2 is selected from the group consisting of H and alkyl.

Figure 4:
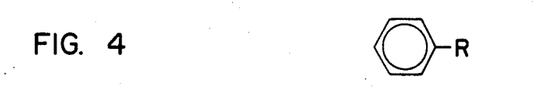
FIGS. 4, 5 and 6 represent classes of compounds suitable as starting materials for the process of the invention.

Starting compounds for the process of producing the compounds represented by FIG. 1 are represented in FIG. 4 in which R has the same definition stated for FIG. 1.

Figure 5:
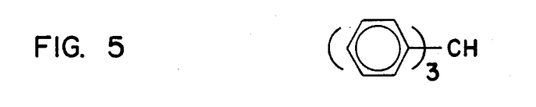
Figure 6:
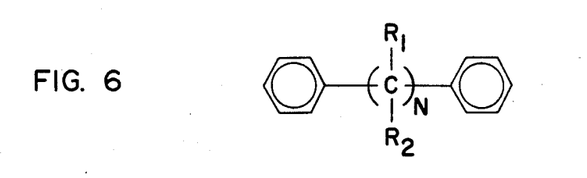
Figure 7:
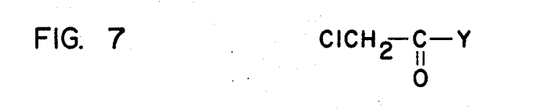
FIG. 7 represents a class of reactants used in step 1 of the process.
Figure 8:
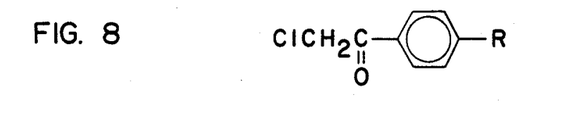
FIGS. 8, 9 and 10 represent classes of compounds produced from the starting materials in step 1 of the process of the invention.
Figure 9:
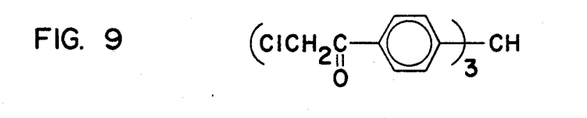
Figure 10:
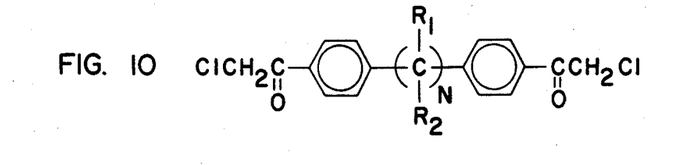

The first step in the process comprises reacting the starting compound with an acyl compound in the presence of a Friedel Crafts catalyst. Suitable acyl compounds for this reaction are represented by FIG. 7 in which Y is selected from the group consisting of —Cl, —OH and This step may be defined as chloroacylating the starting compound. Using the starting materials represented by FIGS. 4, 5 and 6, this step produces compounds represented by FIGS. 8, 9 and 10, respectively, in which n, Y, R, R1 and R2 have the same definitions given above in connection with FIGS. 4, 5, 6 and 7. Each class of compounds represented by FIGS. 8, 9 and 10 has at least one carbonyl group $C{=}O$.

The second step of the process comprises reducing each carbonyl group in the respective compounds produced by the first step. This results in the conversion of each carbonyl group to a hydroxyl group OH and the resulting compound can be defined as an alcohol which corresponds to the carbonyl compound used as the starting material in the second step.

The third step in the process comprises converting each —OH group in the alcohol produced in the second step to an easily eliminatable group such as P-toluene sulfate.

The fourth step in the process comprises eliminating the Cl and the easily eliminatable groups from the compounds produced by the third step under basic conditions to yield compounds represented by FIGS. 1, 2 and 3. Such compounds are known in the prior art as noted heretofore in the The third step in the process comprises converting each —OH group in the alcohol produced in the second step to an easily eliminatable group such as P-toluene sulfate.

The fourth step in the process comprises eliminating the Cl and the easily eliminatable groups from the compounds produced by the third step under basic conditions to yield compounds represented by FIGS. 1, 2 and 3. Such compounds are known in the prior art as noted heretofore in the section entitled BACKGROUND OF THE INVENTION. Persons skilled in this art know that a principal use of these compounds is in aerospace and military applications.

The invention will be illustrated and exemplified by the following specific examples.

SPECIFIC EXAMPLES OF EMBODIMENTS OF THE INVENTION

EXAMPLE 1

Preparation of 4-4'-Diethynyldiphenyl Methane

Step 1, Preparation of 4,4'-Di(2 Chloroacetyl)-Diphenyl Methane

To 6.8 L of dichloromethane in a 12 L flask which had been chilled to −20°, was added 3000 g of anhydrous aluminum chloride (22.5 mole) and the flask placed in a cooling bath. Chloroacetyl chloride (2509 g, 22.2 mole) was added to the rapidly stirred dichloromethane at such a rate to maintain the temperature below 0°. Diphenylmethane (1700 g, 10.1 mole ) was added to the above solution over a period of 1-2 hours at such a rate as to maintain the temperature below 0°.

After the addition was complete, the cooling bath was replaced with a heating mantle and the temperature of the reaction mixture slowly increased to reflux temperature. The solution was refluxed 1.5 hours and then cautiously poured onto approximately 10-15 gal. of crushed ice. After all the ice had melted, 6 L of dichloromethane was added and enough hot water to cause complete dissolution of the yellow solid which had formed. The mixture was stirred vigorously, the layers allowed to separate and the aqueous layer removed. The dichloromethane layer was washed 3 times with 15 L portions of water. Finally, the dichloromethane solution was dried over sodium sulfate overnight with stirring. The dried dichloromethane solution was concentrated and the resulting yellow solid recrystallized from toluene (MP 124–126 deg). The product appeared as a single component by thin layer chromatography (TLC) and was characterized by infrared (IR) and proton nuclear magnetic resonance (NMR) spectroscopies.

TLC DATA: Solvent system:
EtAc/hexane 1.0:1.5
Rf diphenylmethane=0.8
Rf product=0.5

Step 2, Preparation of 4,4'-Di(1-hydroxy-2-chloroethyl)-Diphenyl Methane

A 12 L flask containing 8.3 L of anhydrous methanol (MeOH) was cooled to −20°. The product from above (2788 g, 8.68 mole) was added to the 12 L flask immersed in a cooling bath and vigorously stirred. Sodium borohydride (195.6 g, 5.17 mole) was added in small portions over a period of 2 hr. such that the temperature was maintained below 10°. The solution was stirred an additional 2.5 hr. at 0°-10° and then poured into 48 L of water containing 1.3 L of conc. HCl or 500 ml conc. sulfuric acid and the oily mixture stirred until crystallization of the product was complete. The solid was allowed to settle, the majority of water removed, the product isolated by vacuum filtration and washed several times with hot water. The material was taken up in 6 L of dichloromethane and the solution was dried with anhydrous potassium carbonate. The dichloromethane was removed under vacuum to yield 2629 g (96%) of an oil that crystallized on cooling to room temperature. The light tan product was characterized by IR and NMR and appeared as a single component by TLC (although it is a mixture of diasteriomers). MP 78°–84°.

TLC DATA: Solvent system:
EtAc/hexane 1.0:1.5
Rf product=0.2

Step 3, Preparation of 4.4'-Di(1-Methane Sulfonoxy-2-Chloroethyl)-Diphenyl Methane To a stirred solution of the above product (2646 g, 8.14 moles) in 6.57 L of dimethylformamide (DMF) containing 10 g of di-t-butyl hydroquinone was added over a period of 20 min. 2071 g of methane sulfonyl chloride (18.1 moles). The temperature of the solution increased to 80° and was maintained there by application of heat for 5 hr. At the end of 3 hr. an additional 50 ml of methane sulfonyl chloride was added and at the end of 4.5 hr. 250 g of activated charcoal +100 g of diatomaceous earth was added. Following the 5 hr heating period the activated charcoal and diatomaceous earth were removed by vacuum filtration and the filtrate poured into 48 L of ice water containing 830 g of sodium hydroxide. After vigorous stirring for a few minutes, the product crystallized and settled to the bottom. Most of the water was decanted and the product isolated by vacuum filtration. The solid was washed with a large volume of hot water, crushed to give small granules and air dried in a thin layer for 4 days to yield 2749 g (86%) of product which appeared as a single component by TLC and gave IR and NMR spectra consistant with its structure. MP 82°–91° (diasteriomeric mixture).

TLC DATA: Solvent system:
EtAc/hexane 1.0:1.5
Rf product 0.85

Step 4, Conversion of the Dimesylate to 4,4'-Dimetyldiphenyl Methane (DEDPM)

The dimesylate (2745 g, 5.71 moles) from above was dissolved in 8 L of reagent grade dimethyl sulfoxide (DMSO) containing 10 g of di-t-butyl hydroquinone and stirred vigorously under nitrogen. Sodium methoxide (1800 g, 33.3 moles was added in portions over a period of 1.5 hr. while the temperature was maintained at or below 40° with the aid of an ice bath. After the addition, the reaction was allowed to procede an additional 1.5 hr. at 30°–40°, the solution poured into 36 L of cold water containing some crushed ice and neutralized with conc. HCl. The dark brown oil which formed, crystallized on stirring for a short time and floated to the top of the solution. The product was isolated by vacuum filtration, washed with a large volume of water (room temperature) followed by two washings with 1.5 L 28% ammonium hydroxide and finally several more washings with water. The damp product was dissolved in the minimum amount of dichloromethane approximately 4 L) and extracted several times with water followed by extractions with 6N HCl and 20% potassium carbonate solution. The solution was finally washed with water, dried over sodium sulfate and concentrated under vacuum to yield 1695 g of a red oil (contaminated with DMSO) that crystallized on standing. The product was recrystallized from hexane using activated charcoal to remove color, yielding 1250 g of a yellowish crystalline solid. The solid was stirred overnight with 2.5 L of 20% aqueous methanol (20% water), isolated by vacuum filtration, washed with 1 L of 20% aqueous methanol at −20°, and air dried to yield 1222 g of a light tan product, 100% yield (55.5% overall yield based on diphenyl methane). Approximately 90% pure by C-18 reverse phase HPLC (acetonitrile/water 80:20, 1 ml/min). Proton NMR: 2 proton singlet at 3.0 ppm, 2 proton singlet at 3.83 ppm, 4 proton doublet at 7.15 ppm, 4 proton doublet at 7.35 ppm (approximately 90% pure by NMR). IR: 3285 cm$^{-1}$ (s,sharp), 2110 cm$^{-1}$ (m,sharp). Mass spectrum molecular weight=216 amu (calculated=216.24 amu). MP 49°–55° (reported 61-62)

TLC DATA: Solvent system:
hexane/EtAc 14:1.5
Rf DEDPM=0.72 (2 elutions)

EXAMPLE 2

Preparation of 1,2-(4,4'-Diethynyldiphenyl)Ethane

Step 1, Preparation of 1,2-[4,4'-(2-Chloroacetyl)-Diphenyl]Ethane

Place 90 mL of dichloromethane and 43.0 g (0.32 mole) of anhydrous aluminum chloride in a 250 mL flask and cool in a salt/ice bath. Add 25 mL (0.31 mole) of chloroacetyl chloride to the vigourously stirred mixture at such a rate as to maintain the temperature below 0°. Add a solution of 25.0 g (0.14 mole ) of bibenzyl in 25 mL of dichloromethane at such a rate as to maintain the temperature below 0°. Stir at −3 to 0° for 2 hours and cautiously pour the contents of the flask over 300 mL of crushed ice. Add 100 mL of dichloromethane and stir the mixture vigorously. Allow the layers to separate and remove the lower dichloromethane layer. Extract the aqueous layer with additional dichloromethane (3×50 mL), and dry over anhydrous sodium sulfate. Decant, concentrate and dry the dichloromethane solution and recrystallize the resulting solid from toluene. Yield: 40.2 g (0.12 mole, 86%) of 1,2-[4,4'-di(chloroacetyl)diphenyl]ethane. Single component by C-18 reverse phase HPLC (acetonitrile/water 50:50, 1.0 mL/min). Mp 141°–142°; 1 H NMR (d-6 DMSO, 90 MHz) 3.00 (4H,s), 5.12 (4H,s), 7.42 (4H,d,J=7.8 Hz), 7.91 (4H,d,J=7.8 Hz); EIMS, m/z (relative intensity) 334 (M+, 1.9), 287 (26.0), 286 (17.4), 285 (100), 251 (11.0), 167 (12.3) 133 (5.1), 118 (40.4), 104 (7.6), 92 (12.8), 91 (21.7), 90 (17.4), 89 (9.2), 77 (5.0), 51 (5.9).

Step 2, Preparation of 1,2-[4,4'-Di(1-Hydroxy-2-Chloroethyl)-Diphenyl]Ethane

Place 36.1 g (0.11 mole) of the product of Step 1 and 110 mL of anhydrous methanol in a 250 mL flask. Cool the flask in a salt/ice bath and stir the solution vigorously. Add 2.5 g (0.07 mole) of sodium borohydride in small portions such that the temperature is maintained below 10°. Stir an additional 2.5 hours at 1°–10° and pour the contents of the flask into 600 mL of cold water containing 25 mL of concentrated hydrochloric acid. Stir the mixture until crystallization of the product is complete and isolate the solid by vacuum filtration. Wash the product with water and dry in a vacuum dessicator. Yield: 36.2 g (0.11 mole, 99%) of 1,2-[4,4'-di(1-hydroxy-2-chloroethyl)diphenyl]ethane (diastereomeric mixture).

Single component by C-18 reverse phase HPLC (acetonitrile/water 50:50, 1.0 mL/min) Mp 92°–94°; IR 3390, 3010, 2920, 2860, 1510, 1415, 1330, 1300, 1280, 1200, 1070, 1015, 850, 825, 785, 735, 705 cm$^{-1}$; 1H NMR (d-6 DMSO, 90 MHz) 2.83 (4H, s), 3.66 (4H, m), 4.73 (2H, m), 5.66 (2H, d, J=4.7 Hz), 7.24 (4H, m); EIMS, m/z (relative intensity) 338 (M+, 0.4), 284 (4.7), 274 (7.9), 273 (37.0), 272 (24.1), 271 (100), 266 (5.3), 253 (20.8), 171 (6.2), 169 (19.9), 117 (5.6), 105 (5.5).

Step 3, Preparation of 1,2-[4,4'-Di(1-Methane Sulfonoxy-2-Chloroethyl)-Diphenyl]Ethane Dissolve 34.4 g (0.10 mole) of the product of Step 2 and 0.1 g of di-t-butyl hydroquinone in 85 mL of dimethyl formamide in a 250 mL flask. Add 18.0 mL (0.23 mole) of methane sulfonyl chloride to the rapidly stirred mixture and heat at 80° for 5 hours. After 3 hours, add an additional 1.0 mL (0.01 mole) of methane sulfonyl chloride. At the end of 4.5 hours, add 3.4 g of activated charcoal and 1.5 g of diatomaceous earth. Following the 5 hour heating period, filter the solution through a bed of diatomaceous earth, pour the filtrate into 700 mL of cold water containing 11 g (0.28 mole) of sodium hydroxide and stir vigorously. After crystallization of the product is complete, filter the mixture and wash the solid with copious amounts of water. Dry the product under vacuum. Yield: 37.3 g (0.08 mole, 73%) of 1,2-[4,4'-di(1-methane sulfonoxy-2-chloroethyl)diphenyl]ethane (diastereomeric mixture). Approximately 71% one major component by C-18 reverse phase HPLC (acetonitrile/water 65:35, 1.0 mL/min). Mp 110°–115°; IR 3020, 2940, 2920, 2850, 1905, 1670, 1605, 1510, 1435, 1420, 1350, 1275, 1195, 1185, 940, 840, 715, 675, 635 cm$^{-1}$; 1H NMR (deuterochloroform, 90 MHz) 2.89 (4H, s), 3.93 (4H, m), 4.97 (2H, m), 7.23 (8H, m); EIMS, m/z (relative intensity) 378 (9.4), 376 (24.1), 374 (17.8), 342 (5.2), 341 (6.5), 340 (10.5), 338 (10.2), 304 (4.9), 191 (9.8), 190 (6.2), 189 (64.7), 188 (9.4), 187 (100), 154 (16.0), 153 (20.5), 152 (42.9), 151 (54.5), 117 (35.1).

Step 4, Conversion of the Dimesylate to 1,2-(4,4'-Diethynyldiphenyl)Ethane

Dissolve 37.1 g (0.08 mole) of the dimesylate from Step 3 and 0.1 g of di-t-butyl hydroquinone in 150 mL of reagent grade dimethyl sulfoxide in a 250 mL flask under nitrogen. Vigorously stir the solution and add 23.8 g (0.44 mole) of sodium methoxide in small portions such that the temperature is maintained below 40°. After the addition, stir at 35°–40° for an additional 1.5 hours. Pour the contents of the flask into 500 mL of water containing some crushed ice and neutralize the solution with concentrated hydrochloric acid. After crystallization is complete, filter the mixture and wash the solid with a large amount of water followed by two washings with 50 mL of 28% ammonium hydroxide. Wash again with water and dissolve the damp product in 400 mL of dichloromethane. Wash with water (3×50 mL), 6N hydrochloric acid (1×100 mL), 20% aqueous potassium carbonate solution (1×100 mL), water (1×50 mL), and saturated aqueous sodium chloride solution (1×50 mL). Dry the solution over anhydrous sodium sulfate and concentrate under vacuum. Recrystallize the crude product (23.8 g) from hexane using activated charcoal to remove color. Stir the resulting solid with 50 mL of 80% aqueous methanol overnight, and isolate the product by vacuum filtration. Wash the solid with 10 mL of cold 80% aqueous methanol, and dry under high vacuum. Yield: 18.6 g (0.08 mole, 100%, 62% overall) of 1,2-(4,4'-diethynyldiphenyl)ethane. Approximately 82% pure by C-18 reverse phase HPLC (acetonitrile/water 80:20, 1.0 mL/min). Mp 78°–85° (reported 92–92.5); IR 3255, 3020, 2920, 2105, 1595, 1490, 1445, 1405, 1245, 825, 665, 645, 625 cm$^{-1}$ 1H NMR (deuterochloroform, 90 MHz) 2.85 (4H, s), 3.00 (1H, s), 7.02 (4H, d, J=7.9 Hz), 7.34 (4H, d, J=4.9 Hz); EIMS, m/z (relative intensity) 230 (M+, 36.7), 116 (10.1), 115 (100), 89 (10.0), 65 (8.4), 63 (8.5).

EXAMPLE 3

Preparation of 1,1-(4,4'-Diethynyldiphenyl)Ethane

Step 1, Preparation of 1,1-[4,4'-Di(2-Chloroacetyl)-Diphenyl]Ethane

Place 85 mL of dichloromethane and 34.9 g (0.26 mole) of anhydrous aluminum chloride in a 250 mL flask and cool in a salt/ice bath. Add 20.9 mL (0.26 mole of chloroacetyl chloride to the vigorously stirred mixture at such a rate as to maintain the temperature below 0°. Add 21.0 g (0.12 mole) of 1,1-diphenylethane at such a rate as to maintain the temperature below 0°. Stir at −5° to 0° for 2 hours and pour the contents of the flask onto 300 mL of crushed ice. Extract with dichloromethane (3×50 mLO and combine the organic layers. Wash with water (3×50 mL) and saturated aqueous sodium chloride solution (1×50 mL), and dry over anhydrous sodium sulfate. Decant and concentrate the dried dichloromethane solution to a viscous oil. Approximately 75% one major component by C-18 reverse phase HPLC (actonitrile/water 80:20, 1.0 mL/min.).

Step 2, Preparation of 1,1-[4,4'-Di(1-Hydroxy-2-Chloroethyl)-Diphenyl]Ethane

Place the crude product from Step 1, 50 mL of methanol, and 20 mL of dichloromethane in a 250 mL flask. Cool the flask in a salt/ice bath and stir the mixture vigorously. Add 2.8 g (0.07 mole) of sodium borohydride in small portions such that the temperature is maintained below 10. Stir an additional 2.5 hours and pour the contents of the flask into 800 mL of cold water containig 27 mL of concentrated hydrochloric acid. Extract with dichloromethane (3×50 mL) and combine the organic layers. Wash with water (1×100 mL) and saturated aqueous sodium chloride solution (1×100 mL), and dry over anhydrous sodium sulfate. Decant and concentrate the solution to a viscous oil (diastereomeric mixture). Approximately 75% one major component by C-18 reverse phase HPLC (acetonitrile/water 75:25,·1.0 mL/min).

Step 3, Preparation of 1,1[4,4'-Di(1-Methane Sulfonoxy-2-Chloroethyl)-Diphenyl]Ethane Dissolve the crude product from Step 2 and 0.1 g of di-t-butyl hydroquinone in 100 mL of dimethyl formamide in a 250 mL flask. Add 20.5 mL (0.26 mole of methane sulfonyl chloride to the rapidly stirred mixture and heat at 80° for 5 hours. After 3 hours, add an additional 1.0 mL (0.01 mole) of methane sulfonyl chloride and after 4.5 hours add 4.0 g of activated charcoal and 2.0 g of diatomaceous earth. After the 5 hour heating period, filter the solution through a bed of diatomaceous earth and pour the filtrate into 600 mL of cold water containing 13.0 g (0.33 mole) of sodium hydroxide. Extract with dichloromethane (1×50 mL) and combine the organic layers. Wash with water (3×50 mL) and saturated aqueous sodium chloride solution (1×50 mL), and dry over anhydrous sodium sulfate. Decant and concentrate to a viscous oil (diastereomeric mixture). Approximately 60% one major component by C-18 reverse phase HPLC (acetonitrile/water 75:25, 1.0 mL/min).

Step 4, Conversion of the Crude Dimesylate to 1,1-(4,4'-Diethynyldiphenyl)Ethane Dissolve the crude product of Step 3 and 0.1 g of di-t-butyl hydroquinone in 120 mL of reagent grade dimethyl sulfoxide in a 250 mL flask under nitrogen. Vigorously stir the solution and add 27.0 g (0.50 mole) of sodium methoxide in small portions such that the temperature of the mixture is maintained below 40°. After the addition, stir at 37°–40 ° for an additional 2 hours and pour the contents of the flask into 500 ml of water containing some crushed ice. Neutralize the solution with concentrated hydrochloric acid, extract with dichloromethane (3×50 mL), and combine the organic layers. Wash with water (3×50 mL), 10% aqueous hydrochloric acid (1×50 mL), 20% aqueous potassium carbonate solution (1×50 mL), water (1×50 mL), and saturated aqueous sodium chloride solution (1×50 mL), and dry over anhydrous sodium sulfate. Decant and concentrate the dried dichloromethane solution to a viscous oil (23.1 g), and distill the crude material under reduced pressure. Yield: 16.4 g (0.07 mole, 60% overall) of 1,1-(4,4'-diethynyldiphenyl)ethane. Approximately 87% pure by C-18 reverse phase HPLC (acetonitrile/water 80:20, 1.0 mL/min). Bp 113°(0.02 mm Hg); IR 3305, 3045, 2985, 2950, 2895, 2110, 1610, 1505, 1455, 1415, 1375, 1235, 1115, 1060, 1045, 1015, 840 cm$^{-1}$; 1H NMR (deuterochloroform, 60 MHz) 1.55 (3H, d, J=7.2 Hz), 3.04 (2H, s), 4.10 (1H, q, J=7.2 Hz), 1.17 (4H, d, J=8.8 Hz), 7.58 (4H, d, J=8.8 Hz); EIMS m/z (relative intensity) 230 (M+, 32.3), 215 (100), 213 (18.4), 189 (12.7), 128 (13.1), 115 (11.6), 77 (17.4), 75 (15.4), 63 (13.3), 51 (21.3), 50 (13.3), 44 (13.7).

EXAMPLE 4

Preparation of Tris(4-Ethynylphenyl)Methane

Step 1 Preparation of Tris [4-(2-Chloroacetyl)-Phenyl]Methane

Place 90 mL of dichloromethane and 36.0 g (0.27 mole) of anhydrous aluminum chloride in a 250 mL flask and cool in a salt/ice bath. Add 21.5 mL (0.27 mole) of chloroacetyl chloride to the vigorously stirred mixture at such a rate as to maintain the temperature below 0°. Add 20.0 g (0.08 mole) of triphenymethane dissolved in 35 mL of dichloromethane such that the temperature is maintained below 0°. Stir at −5° to 0° for 2 hours and slowly warm to reflux for an additonal 2 hours. Pour the contents of the flask over 300 mL of crushed ice, extract with dichloromethane (3×50 mL), and combine the organic layers. Wash with water (3×50 mL) and saturated aqueous sodium chloride solution (1×50 mL), and dry over anhydrous sodium sulfate. Decant and concentrate the solution to a viscous oil. Approximately 75% one major component by C-18 reverse phase HPLC (acetonitrile/water 80:20, 1.0 mL/min).

Step 2, Preparation of Tris[4-(1-Hydroxy-2-chloroethyl)-Phenyl]Methane

Place the crude product of Step 1, 50 mL of anhydrous methanol, and 25 mL of dichloromethane in a 250 mL flask and cool in a salt/ice bath. Vigorously stir the solution and add 3.1 g (0.08 mole) of sodium borohydride in small portions such that the temperature is maintained below 10°. Stir an additional 2.5 hours and pour the contents of the flask into 600 ml of cold water containing 29 mL of concentrated hydrochloric acid. Extract the solution with dichloromethane (3×50 mL) and combine the organic layers. Wash with water (3×50 mL) and saturated aqueous sodium chloride solution (1×50 mL), and dry over anhydrous sodium sulfate. Decant and concentrate the solution to a viscous oil (diastereomeric mixture). Approximately 75% one major component by C-18 reverse phase HPLC (acetonitrile/water 75:25, 1.0 mL/min).

Step 3, Preparation of Tris[4-(1-Methane Sulfonoxy-2-Chloroethyl)-Phenyl]Methane Dissolve the crude product from Step 2 and 0.1 g of di-t-butyl hydroquinone in 80 mL of dimethyl formamide in a 250 mL flask. Add 21.1 mL (0.27 mole) of methane sulfonyl chloride to the rapidly stirred mixture and heat at 80° for 5 hours. After 3 hours, add an additional 1.0 mL (0.01 mole) of methane sulfonyl chloride. After 4.5 hours, add 4.0 g of activated charcoal and 2.0 g of diatomaceous earth. Following the 5 hour heating period, filter the solution through a bed of diatomaceous earth and pour the filtrate into 600 mL of cold water containing 13.0 g 0.33 mole) of sodium hydroxide. Extract with dichloromethane ( 3×50 mL) and combine the organic layers. Wash with water (3×50 mL), and dry over anhydrous sodium sulfate. Decant and concentrate the solution to a viscous oil (diastereomeric mixture). Approximately 65% one major component by C-18 reverse phase HPLC (acetonitrile/water 85:15, 1.0 mL/min).

Step 4, Conversion of the Crude Trimesylate to Tris(4-Ethynylphenyl)Methane

Dissolve the crude product from Step 3 and 0.1 g of di-t-butyl hydroquinone in 100 mL of reagent grade dimethyl sulfoxide in a 250 mL flask under nitrogen. Vigorously stir the solution and add 29.3 g (0.54 mole) of sodium methoxide in small portions at such a rate as to maintain the temperature below 40°. After the addition, stir at 38°–42° for an additional 2 hours and pour the contents of the flask into 600 mL of water containing some crushed ice. Neutralize the solution with concentrated hydrochloric acid, extract with dichloromethane (3×50 mL), and combine the organic layers. Wash with water (3×50 mL), 10% aqueous hydrochloric acid solution (1×50 mL), 24% aqueous potassium carbonate solution, water (1×50 mL), and saturated aqueous sodium chloride solution (1×50 mL), and dry over anhydrous sodium sulfate. Decant and concentrate to a viscous oil. Purify the crude material by Silica Gel chromatography (elution with ethyl acetate/hexanes 2.5:97.5). Yield: 15.4 g (0.05 mole, 59% overall) of tris-4-ethynylphenyl methane as an opalescent glass. Approximately 88% pure by C-18 reverse phase HPLC (acetonitrile/water 85:15, 1.0 mL/min). IR 3300, 3030, 2100, 1608, 1560, 1500, 1416, 1240, 1110, 1015, 860, 790 cm$^{-1}$, 1H NMR (deuterchloroform, 90 MHz) 3.03 (3H, s), 5.48 (1H, s), 7.00 (6H, d, J=8.1 Hz), 7.40 (6H, d, J=8.1 Hz); EIMS m/z (relative intensity) 317 (26.4), 316 (M+, 100), 315 (38.2), 215 (82.6), 214 (38.9), 613 (93.7), 189 (36.7), 51 (31.2), 44 (28.9).

EXAMPLE 5

Preparation of 4-Ethynyl Toluene

Step 1, Preparation of 4-(2-Chloroacetyl)Toluene

Place 80 mL of dichloromethane and 31.9 g (0.24 mole) of anhydrous aluminum chloride in a 250 mL flask and cool in a salt/ice bath. Add 19.0 mL (0.24 mole) of chloroacetyl chloride to the vigorously stirred mixture at such a rate as to maintain the temperature below 0°. Add 20.0 g (0.22 mole) of toluene such that the temperature of the solution is maintained below 0°. Stir at −5° to 0° for 2 hours, heat at reflux for 2.5 hours, and pour the contents of the flask over 300 mL of crushed ice. Extract with dichloromethane (3×50 mL) and combine the organic layers. Wash with water (3×50 mL) and saturated aqueous sodium chloride solution (1×50 mL), and dry over anhydrous sodium sulfate. Decant and concentrate the solution to an oil. Single component by C-18 reverse phase HPLC (acetonitrile/water 80:20, 1.0 mL/min).

Step 2, Preparation of 4-(1-Hydroxy-2-Chloroethyl)-Toluene

Place the crude product from Step 1, 50 mL of anhydrous methanol, and 25 mL of dichloromethane in a 250 mL flask. Cool the flask in a salt/ice bath and stir the solution vigorously. Add 2.5 g (0.07 mole) of sodium borohydride in small portions such that the temperature is maintained below 10°. Stir for an additional 2.5 hours and pour the contents of the flask into 600 mL of cold water containing 25 mL of concentrated hydrochloric acid. Extract with dichloromethane (3×50 mL) and combine the organic layers. Wash with water (3×50 mL) and saturated aqueous sodium chloride solution (1×50 mL), and dry over anhydrous sodium sulfate. Decant and concentrate the solution to an oil. Approximately 99% pure by C-18 reverse phase (acetonitrile/water 75:25, 1.0 mL/min).

Step 3, Preparation of 4-(1-Methane Sulfonoxy-2-Chloroethyl)Toluene

Dissolve the crude product of Step 2 and 0.1 g of di-t-butyl hydroquinone in 175 mL of dimethyl formamide in a 250 mL flask. Add 18.6 mL (0.24 mole) of methane sulfonyl chloride to the rapidly stirred mixture and heat at 80° for 5 hours. After 3 hours, add 1.0 mL (0.01 mole) of additional methane sulfonyl chloride. After 4.5 hours, add 5.0 g of activated charcoal and 2.5 g of diatomaceous earth. Following the 5 hour heating period, filter the solution through a bed of diatomaceous earth and pour the filtrate into 600 mL of cold water containing 11.5 g (0.29 mole) of sodium hydroxide. Extract with dichloromethane (3×50 mL) and combine the organic layers. Wash with water (3×50 mL) and saturated aqueous sodium chloride solution (1×50 mL), and dry over anhydrous sodium sulfate. Decant and concentrate the solution to an oil. Approximately 80% pure by C-18 reverse phase HPLC (acetonitrile/water 85:15, 1.0 mL/min).

Step 4, Conversion of the Mesylate to 4-Ethynyl Toluene

Dissolve the crude mesylate of Step 3 and 0.1 g of di-t-butyl hydroquinone in 100 mL of reagent grade dimethyl sulfoxide in a 250 mL flask under nitrogen. Vigorously stir the solution and add 24.0 g (0.44 mole) of sodium methoxide in small portions such that the temperature is maintained below 40°. After the addition, stir at 35°–40° for an additional 2.5 hours and pour the contents of the flask into 600 mL of cold water containing some crushed ice. Neutralize the solution with concentrated hydrochloric acid, extract with dichloromethane (3×50 mL), and combine the organic layers. Wash with water (3×50 mL), and 10% aqueous hydrochloric acid solution, 20% aqueous potassium carbonate solution (1×50 mL), and dry over anhydrous sodium sulfate. Decant and concentrate the solution to an oil. Distill the residue under reduced pressure. Yield 16.0 g (0.14 mole, 63% overall) of 4-ethynyl toluene. Single component by C-18 reverse phase HPLC (acetonitrile/water 80:20, 1.0 mL/min). Bp 79°–81° (37 mm Hg); IR 3325, 3045, 2940, 2110, 1655, 1510, 1570, 1510, 1450, 1380, 1240, 1175, 1110, 1100, 1040, 1020, 950, 820 cm$^{-1}$; 1H NMR (deuterchloroform, 60 MHz) 2.28 (3H, s), 3.00 (1H, s), 7.08 (2H, d, J=8.6 Hz), 7.53 (2H, d, J=8.6 Hz); EIMS, m/z (relative intensity) 117 (9.5), 116 (M+, 86.5), 115 (100), 89 (15.5), 63 (17.1), 62 (9.3), 51 (9.5), 50 (12.5), 44 (28.2). EXAMPLE 6

Preparation of 2,2-(4,4-Diethynyldiphenyl)Propane

Step 1, Preparation of 2,2-[4,4'-Di(2-Chloroaecetyl)-Diphenyl]Propane

Place 100 mL of dichloromethane and 39.1 g (0.29 mole) of anhydrous aluminum chloride in a 250 mL flask and cool in a salt/ice bath. Add 23.3 mL (0.28 mL) of chloroacetyl chloride to the rapidly stirred mixture at such a rate as to maintain the temperature below 0°. Add 24.5 g (0.13 mole) of 2,2-diphenyl propane such that the temperature is maintained below 0°. Stir at −3° to 0° for an additional 2 hours and pour the contents of the flask over 300 mL of crushed ice. Extract with dichloromethane (3×50 mL) and combine the organic layers. Wash with water (3×50 mL) and saturated aqueous sodium chloride solution (1×50 mL), and dry over anhydrous sodium sulfate. Decant and concentrate the solution. Recrystallize the crude product from toluene. Yield: 22.4 g (0.06 mole, 51%) of 2,2-[4,4'-di(2-chloroacetyl)diphenyl]propane. Single component by C-18 reverse phase HPLC (acetonitrile/water 80:20, 1.5 mL/min). mp 137°–138.5°.

Step 2, Preparation of 2,2-[4,4'-Di(1-Hydroxy-2-Chloroethyl)-Diphenyl]Propane

Place 22.0 g (0.06 mole) of the product of Step 1, 30 mL of anhydrous methanol, and 50 mL of dichloromethane in a 250 ml flask. Cool the flask in a salt/ice bath and stir vigorously. Add 1.44 g (0.04 mole) of sodium borohydride in small portions such that the temperature is maintained below 10°. Stir at 0°–10° for 2.5 hours, and pour the contents of the flask into 500 mL of cold water containing 15 mL of concentrated hydrochloric acid. Extract with dichloromethane (3×50 ml) and combine the organic layers. Wash with water (3×50 mL) and saturated aqueous sodium chloride solution (1×50 mL), and dry over anhydrous sodium sulfate. Decant and concentrate the solution to an oil (diastereomeric mixture). Single component by C-18 reverse phase HPLC (acetonitrile/water 80:20, 1.0 mL/min).

Step 3, Preparation of 2,2-[4,4'-Di(1-Methane Sulfonoxy-21-Chloroethyl)-Diphenyl]Propane Dissolve the crude product of Step 2 and 0.1 g of di-t-butyl hydroquinone in 60 mL of dimethyl formamide in a 250 mL flask. Add 11.4 mL (0.15 mole) of methane sulfonyl chloride to the rapidly stirred mixture and heat at 80° for 5 hours. After 3 hours, add an additional 1.0 mL (0.01 mole) of methane sulfonyl chloride.

After 4.5 hours, add 2.5 g of activated charcoal and 1.0 g of diatomaceous earth. Following the 5 hour heating period, filter the solution through a bed of diatomaceous earth and pour the filtrate into 500 mL of cold water containing 8.0 g (0.20 mole) of sodium hydroxide. Extract with dichloromethane (3×50 mL) and combine the organic layers. Wash with water (3×50 mL) and saturated aqueous sodium chloride solution (1×50 mL), and dry over anhydrous sodium sulfate. Decant and concentrate the solution to an oil (diastereomeric mixture). Approximately 75% one major component by C-18 reverse phase HPLC (acetonitrile/water 80:20, 1.5 mL/min).

Step 4, Conversion of the Crude Dimesylate to 2,2-(4,4'-Diethynyldiphenyl)Propane Dissolve the crude dimesylate of Step 3 and 0.1 g of di-t-butyl hydroquinone in 90 mL of reagent grade dimethyl sulfoxide in a 250 ml flask under nitrogen. Vigorously stir the solution and add 16.8 g (0.31 mole) of sodium methoxide in small portions such that the temperature is maintained below 40°. After the addition, stir at 35°–40° for an additional 4 hours and pour the contents of the flask into 500 ml of water containing some crushed ice. Neutralize the solution with concentrated hydrochloric acid, extract with dichloromethane (3×50 mL), and combine the organic layers. Wash with water (3×50 mL), 10% aqueous hydrochloric acid solution (1×50 mL), 20% aqueous potassium carbonate solution (1×50 mL), water (1×50 mL), and saturated aqueous sodium chloride solution (1×50 mL), and dry over anhydrous sodium sulfate. Decant and concentrate the solution. Recrystallize the residue from hexanes using activated charcoal to remove color. Stir the solid with 50 mL of 80% aqueous methanol and isolate the product by vacuum filtration. Wash the solid with 10 mL of cold 80% aqueous methanol and dry in a vacuum dessicator. Yield: 11.3 g (0.05 mole, 37% overall) of 2,2-(4,4'-diethynyldiphenyl)propane. Approximately 93% pure by C-18 reverse phase HPLC (acetonitrile/water 80:20, 1.5 mL/min). Mp 86°–89°; IR 3265, 3025, 2965, 2860, 2110, 1670, 1600, 1495, 1465, 1400, 1365, 1270, 1225, 1100, 1080, 1015, 840, 745, 640 cm$^{-1}$; 1H NMR (deuterochloroform, 60 MHz) 1.57 (6H, s), 2.97 (2H, s), 7.13 (4H, d, J=8.7 Hz), 7.40 (4H, d, J=8.7 Hz); EIMS, m/z (relative intensity) 244 (M+, 21.6), 230 (19.9), 229 (100), 127 (26.9), 115 (9.8), 101 (12.1), 77 (11.1), 75 (9.6), 51 (12.1), 44 (33.8).

EXAMPLE 7

Preparation of 4-Ethynlbiphenyl

Step 1, Preparation of 4-(2-Chloroacetyl)-Biphenyl

To 30 ml of 1,2-dichloromethane chilled to −20° was added 4.66 g of aluminum chloride (0.035 mole) followed by 3.95 g (0.035 mole) of chloroacetyl chloride. The temperature was maintained below 0° during both additions. Biphenyl (5 g, 0.032 mole) in 15 ml of 1,2-dichloroethane was added to the above solution over a period of 20 min., the reaction mixture stirred an additional 15 min. and poured over 100 g of crushed ice. Dichloromethane (100 ml) was added, the phases separated and the organic phase vacuum filtered to remove a small amount of insoluable material. Drying of the organic layer with sodium sulfate followed by recrystallization of the solid left on removal of solvent yielded 6.31 g of product (84.4%). Single component by C-18 reverse phase HPLC (acetonitrile/water 80:20, 1 mll/min.). Proton NMR: 2 protonsinglet at 4.65 ppm and 9 proton multiplet at 7.3–8.15 ppm.

Step 2, Preparation of 4-(1-Hydroxy-2-Chloroethyl)-Biphenyl

The product from above (6.31 g, 0.027 mole) was suspended in 70 ml of ethanol and the stirred suspension cooled to −15°. Sodium borohydride (0.51 g, 0.014 mole) was added in portions over a period of 25 min. while maintaining the temperature of the reaction below 5°. After stirring for an additional 0.5 hr. the solution was poured into 100 ml of ice water containing 10 ml conc. HCl. The oily product was extracted into 150 ml of dichloromethane (3×50 ml), dried with sodium sulfate and concentrated under vacuum to yield 6.3 g (99%) of a light yellow viscous oil (single component by TLC, Rf=0.45 in hexane/EtAc 1.5:1.0).

Step 3, Preparation of 4-(1-Methane Sulfonoxy-2-Chloroethyl)-Biphenyl

To a stirred solution of 6.01 g (0.026 mole) of the chlorohydrin from above in 30 ml of dimethyl acetamide (DMAc) was added dropwise over a period of 10 min. 3.44 g (0.03 mole) of methane sulfonyl chloride. The temperature was increased to 60° by the application of heat and maintained there for 7.5 hr. After the reaction period, the solution was poured ito 100 ml of cold water containing 10 g of sodium carbonate, and the resulting solid, isolated by vacuum filtration, was washed with a large volume of water, air dried and recrystallized twice from isopropyl alcohol utilizing activated charcoal to yield 5.11 g (63%) of a yellow crystalline material which appeared as a single component by TLC (Rf=0.9 in hexane/ethyl acetate 1.5:1.0).

Step 4, Conversion of the Chloromesylate to 4-Ethynyl-biphenyl

To a solution of 2.1 g (0.0068 mole) of the chloromesylate in 20 ml of DMSO containing 0.02 g of di-t-butyl hydroquinone was added with cooling 1.4 g (0.02 mole) of sodium ethoxide over a period of 20 min. The reaction was allowed to procede at room temperature 1 hr. and then poured into 75 ml of ice water. The solution was neutralized with dilute HCl, filtered to remove product, the product washed with a large volume of water, air dried, and recrystallized from hexane to yield 1.2 g (99%) of 4-ethynylbiphenyl (overall yield=52% based on starting biphenyl). MP=83°-85°. Single component by C-18 reverse phase HPLC (acetonitrile/water 80:20, 1 ml/min). IR: 3260 cm.$^{-1}$. (s, sharp), 2130 cm.$^{-1}$. (m, sharp). Mass spectrum molecular weight=178 amu (calculated=178.2 amu).

Although the invention has been described and illustrated by reference to some specific examples of preferred embodiments of the invention, it will be understood and appreciated by those skilled in this art that modifications, variations and substitutions of other compounds may be made without departing from the scope of the invention as defined in the claims hereof.

Having thus described and illustrated the invention, what is claimed is:

1. The process of producing ethynyl aromatic compounds from the group consisting of the classes having structural formulas represented by the following formulas (1), (2) and (3):

(1)

in which R is selected from the group H, Alkyl and Phenyl, (2)

(3)

in which $R_1$ and $R_2$ are selected from the group H and alkyl and n is 1, 2, 3 or 4, which comprises:

A. reacting a compound selected from the classes represented by the following formulas (4), (5) and (6):

(4)

in which R has the same significance as in Formula (1), (5)

(6)

in which $R_1$, $R_2$ and n have the same significance as in Formula (3), with an acetyl compound selected from the class represented by the following formula (7):

(7)

in which Y is selected from the group —Cl, —OH and in the presence of a Friedel-Crafts catalysts to yield a compound of the class represeneted by the following formulas (8), (9) and (10):

(8)

in which R has the same significance as in Formula (1).

(9)

(10)

in which $R_1$, $R_2$ and n have the same significance as in Formula (3),

B. reducing each carbonyl group in said compounds (8), (9) and (10) to yield a corresponding alcohol, C. converting each hydroxy group in said alcohol to an easily eliminatable group when subjected to step D, and D. eliminating the chloride and the easily eliminatable group from the reaction product of step C under basic conditions.

2. The process of producing ethynyl aromatic compounds from the group consisting of the classes represented by structural formulas (1), (2) and (3) which follow:

(1)

in which R is selected from the group H, alkyl and phenyl, (2)

(3)

in which $R_1$ and $R_2$ are selected from the group H and alkyl and n is 1, 2, 3 or 4, and which comprises four steps:

A. chloracetylating a compound selected from the classes represented by the structural formulas (4), (5) and (6) which follow:

(4)

in which R has the same significance as in Formula (1), (5)

(6)

in which $R_1$, $R_2$ and n have the same significance as in Formula (3),

B. reducing each carbonyl group in the reaction product of step A to a hydroxyl group;

C. converting each hydroxyl group in the reaction product of step B to an easily eliminatable group, and (D) converting the reaction product of step C to a compound within a class represented by structural formulas (1), (2) and (3) by eliminating chlorine and the easily eliminatable groups under basic conditions.

3. The process of preparing 4,4'-diethynyldiphenyl methane which comprises the following four steps:

A. preparing 4,4'-di(2-chloroacetyl)-diphenyl methane by a Friedel-Crafts reaction of diphenyl methane with chloroacetyl chloride as the chloroacetylating agent and recrystallizing the reaction product to purify it, B. preparing 4,4'-di(1-hydroxy-2-chloroethyl)-diphenyl methane from the purified reaction product of step A by reacting it with sodium borohydride and crystallizing the reaction product, C. preparing 4,4'-di(1-methane sulfonoxy-2-chloroethyl)-diphenyl methane by reacting the reaction product of step B with methane sulfonyl chloride in the presence of a suitable solvent, and D. converting the product prepared in step C to 4,4'-diethynyldiphenyl methane with sodium methoxide in a suitable solvent.

4. The process of preparing 1,2-(4,4'-diethynyldiphenyl)ethane which comprises:
   A. reacting bibenzyl with chloroacetyl chloride in the presence of a Friedel-Crafts catalyst in a suitable solvent to produce 1,2-[4,4'-(2-chloroacetyl)-diphenyl]ethane,
   B. reacting the product of step A with sodium borohydride in a suitable solvent to produce 1,2-[4,4'-di(1-hydroxy-2-chloroethyl)-diphenyl]ethane,
   C. reacting the product of step B with methane sulfonyl chloride in the presence of a suitable solvent to produce 1,2-[4,4'-di(1-methane sulfonoxy-2-chloroethyl)-diphenyl]ethane, and
   D. Reacting the product of step C with sodium methoxide in a suitable solvent and neutralizing the solution to produce 1,2-[4,4'diethynyldiphenyl]ethane.

5. The process of producing 1,1-(4,4'-diethynyldiphenyl)ethane which comprises:
   A. reacting 1,1-diphenylethane with chloroacetyl chloride in the presence of a Friedel-Crafts catalyst in a suitable solvent to produce 1,1-[4,4'di(2-chloroacetyl)-diphenyl]ethane,
   B. Reacting the product of step A with sodium borohydride in a suitable solvent to produce 1,1-[4,4'-di(1-hydroxy-2-chloroethyl)-diphenyl]ethane,
   C. Reacting the product of step B with methane sulfonyl chloride to produce 1,1-[4,4'-Di(1-methane sulfonoxy-2-chloroethyl)-diphenyl]ethane, and
   D. Reacting the product of step C with sodium methoxide in a suitable solvent and neutralizing the solution to produce 1,1-(4,4'-diethynyldiphenyl)ethane.

6. The process of producing tris(4-ethynylphenyl)methane which comprises:
   A. Reacting triphenylmethane with chloroacetyl chloride to produce tris[4-(2-chloroacetyl)-phenyl]methane,
   B. Reacting the product of step A with sodium borohydride in a suitable solvent to produce tris[4-(1-hydroxy-2-chloroethyl)-phenyl]methane,
   C. Reacting the product of step B with methane sulfonyl chloride in a suitable solvent to produce tris[4-(1-methane solfonoxy-2-chloroethyl)-phenyl]methane, and
   D. Reacting the product of step C with sodium methoxide in a suitable solvent and neutralizing the solution to produce tris(4-ethynylphenyl)methane.

7. The process of producing 4-ethynyl toluene which comprises:
   A. reacting toluene with chloroacetyl chloride in the presence of a Friedel-Crafts catalyst in a suitable solvent to produce 4-(2-chloroacetyl)toluene,
   B. Reacting the product of step A with sodium borohydride in a suitable solvent to produce 4-(1-hydroxy-2-chloroethyl)toluene,
   C. Reacting the product of step B with methane sulfonyl chloride in a suitable solvent to produce 4-(1-methane sulfonoxy-2-chloroethyl)toluene, and
   D. Reacting the product of step C with sodium methoxide in a suitable solvent and neutralizing the solution to produce 4-ethynyl toluene.

8. The proess of producing 2,2'-(4,4'-diethynyldiphenyl)propane which comprises:
   A. reacting 2,2-diphenyl propane in the presence of a Friedel-Crafts catalyst in a suitable solvent with chloroacetyl chloride to produce 2.2-[4.4'-di(2-chloroacetyl)-diphenyl]propane,
   B. reacting the product of step A with sodium borohydride in a suitable solvent to produce 2,2'-[4.4'-di(1-hydroxy-2-chloroethyl)-diphenyl]propane,
   C. reacting the product of step B with methane sulfonyl chloride in a suitable solvent to produe 2,2'-[4,4'-di(1methane sulfonoxy-2-chloroethyl)-diphenyl]propane, and
   D. Reacting the product of step C with sodium methoxide in a suitable solvent and neutralizing the solution to produce 2,2'-(4,4'-diethynyldiphenyl)-propane.

9. The process of producing 4-ethynylbiphenyl which comprises:
   A. reacting biphenyl in the presence of a Friedel-Crafts catalyst in a suitable solvent with chloroacetyl chloride to produce 4-(2-chloroacetyl)-biphenyl,
   B. reacting the product of step A with sodium borohydride in a suitable solvent to produce 4-(1-hydroxy-2-chloroethyl)-biphenyl,
   C. reacting the product of step B with methane sulfonyl chloride in a suitable solvent to produce 4-(1-methane sulfonoxy-2-chloroethyl)-biphenyl, and
   D. reacting the product of step C with sodium ethoxide in a suitable solvent and neutralizing the solution to produce 4-ethynylbiphenyl.

10. The process of preparing 4,4'-diethynyldiphenyl membrane which comprises the following four steps:
   A. preparing 4,4'-di(2-chloroacetyl)-diphenyl methane by a Friedel-Crafts reaction of diphenyl methane with chloroacetyl chloride as the chloracetylating agent and recrstallizing the reaction product to purify it,
   B. preparing 4,4'-di(1-hydroxy-2-chloroethyl)-diphenyl methane from the purified reaction product of step A by reacting it with sodium borohydride and crystallizing the reaction product,
   C. preparing 4,4'-di(methane sulfonoxy-2-chloroethyl)-diphenyl methane by reacting the reaction product of step B with methane sulfonyl chloride in a solvent comprising dimethylformamide and di-t-butyl hydroquinone, and
   D. converting the product prepared in step C to 4,4'-diethynyldiphenyl methane with sodium methoxide in a solvent comprising dimethyl sulfoxide and di-t-butyl hydroquinone.

* * * * *